United States Patent [19]

Porcelli

[11] Patent Number: 4,934,355
[45] Date of Patent: Jun. 19, 1990

[54] FOOT BRACE

[76] Inventor: Timothy W. Porcelli, 743 Brummel, Evanston, Ill. 60202

[21] Appl. No.: 250,710

[22] Filed: Sep. 28, 1988

[51] Int. Cl.[5] ............................................. A61F 5/00
[52] U.S. Cl. ............................................. 128/80 H
[58] Field of Search ............... 128/80 H, 80 E, 80 F

[56] References Cited

U.S. PATENT DOCUMENTS

| | | | |
|---|---|---|---|
| 3,064,644 | 11/1962 | Patterson | 128/80 H |
| 3,732,861 | 5/1973 | Lehneis | 128/80 E |
| 3,779,654 | 12/1973 | Horne | 128/80 H |
| 3,805,773 | 4/1974 | Sichau | 128/80 E |
| 4,289,122 | 9/1981 | Mason et al. | 128/80 H |
| 4,494,534 | 1/1985 | Hutson | 128/80 F |
| 4,517,968 | 5/1985 | Greene et al. | 128/80 H |
| 4,665,904 | 5/1987 | Lerman | 128/80 F |
| 4,738,252 | 4/1988 | Friddle et al. | 128/80 H |
| 4,771,768 | 9/1988 | Crispin | 128/80 H |

FOREIGN PATENT DOCUMENTS 8707498 12/1987 PCT Int'l Appl. ............... 128/80 H Primary Examiner—Edgar S. Burr
Assistant Examiner—Huong Q. Pham
Attorney, Agent, or Firm—William P. Porcelli

[57] ABSTRACT

A foot brace for correcting paralysis caused by cerebral vascular impairment. The brace has a heel cup for positioning around the wearer's heel and a portion of the wearer's foot and clamp means flexibly connected to and extending upward from the heel cup to an elevation where it may be clamped on the wearer's leg immediately above the wearer's ankle. A binder encircles at least portions of the clamp means to enable the clamp means to be tightened around the leg.

14 Claims, 1 Drawing Sheet

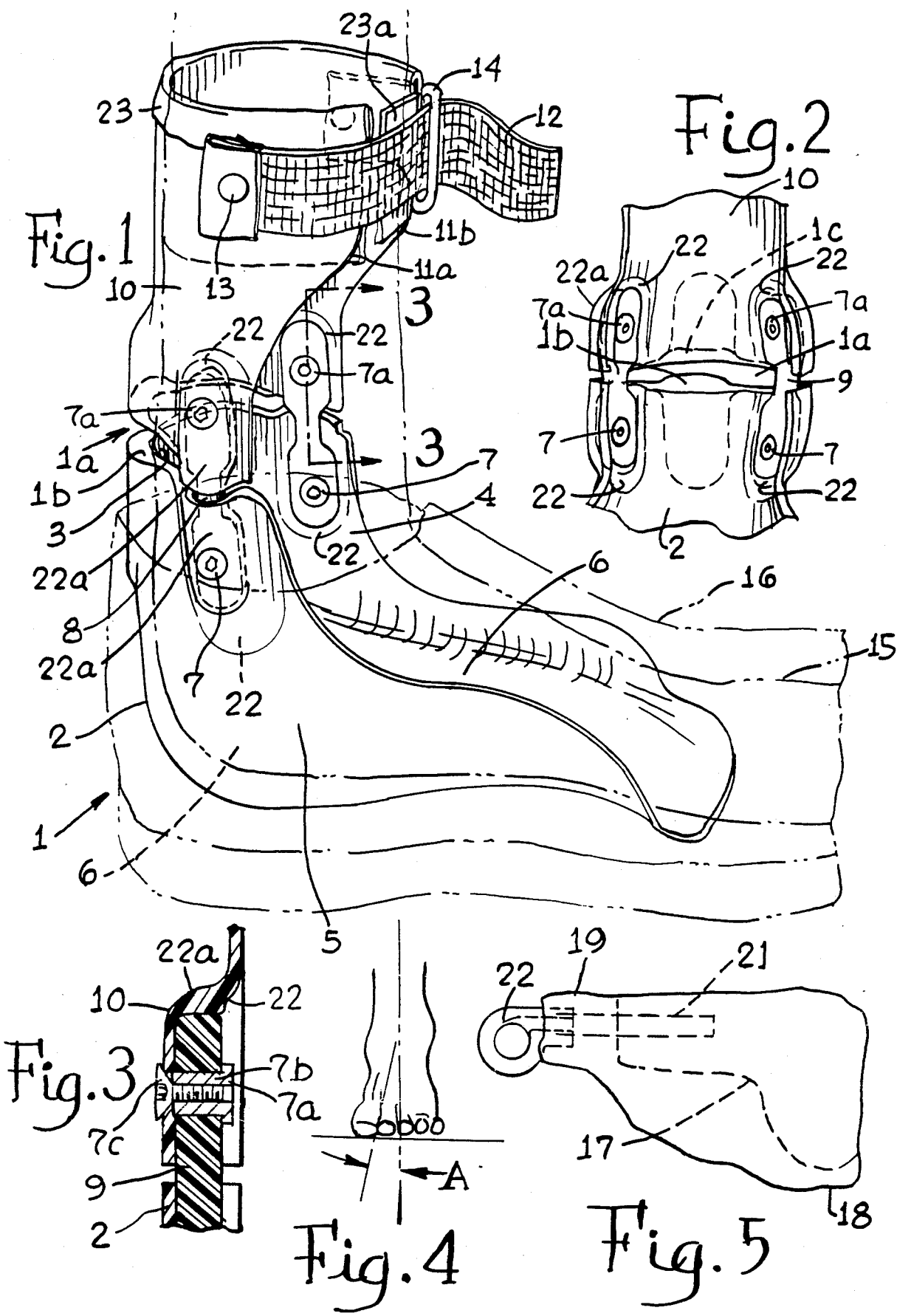

FOOT BRACE

BACKGROUND OF THE INVENTION

This invention relates to the art of foot braces and, in particular, to foot braces especially suited for patients suffering certain physical paralysis of portions of the body due to cerebral vascular impairment, such as suffered by stroke victims.

When a patient suffers cerebral vascular impairment due to an accident or a stroke, or other causes, a common result is some degree of physical paralysis. A theory of what happens is that the impairment of the brain results in interruption or elimination of certain signals to the brain which are ordinarily transmitted from the affected body parts through neurological connections to the brain. The parts of the body affected are determined by which parts of the brain become impaired. For example, it is well known that the right side of the brain generally controls the left side of the body, and conversely. As a result, sense of touch may be diminished or eliminated and certain muscles may become substantially inactive and the patient may lose ability to adequately control movements of parts of the body on one side of the body, or both. In one extreme, a patient might completely lose the sense of where a limb is in space.

In other examples, physical impairment may manifest itself as inability to straighten the knee from a partially flexed or hyperextended position, inability to properly flex the ankle through its normal angular movement, or inability to stand in a normal erect position or move an arm or leg through its normal angular movement, or combinations of these. A typical stroke victim condition may involve some degree of paralysis of an entire side of the body with a foot dragging in a downward hanging position, an arm bent with the hand curled in a modified fist position, and a curved spine causing the patient to tilt from an erect position.

The traditional remedy for some of these deficiencies is to employ rigid bracing to force retain the body parts in a fixed and sometimes abnormal alignment of the body parts to allow the patient somewhat improved but limited use of the limbs or body parts. It would be common for a rigid brace to be applied to a dragging foot to force retain it in a position approximately perpendicular to the leg and thereby allow the patient to better use the leg for walking. Such a brace would not, however, allow any movement or flexure of the ankle as is necessary for a normal walking gait.

Another disadvantage of a rigid brace, aside from the limitations it imposes on normal limb movement, is that the forced immobility of the limb prevents use of the limb muscles and muscle atrophy and further limb disfunction may result. In cases where the muscles involved have no proprioception or neurological connections to the brain due to the nature of the cerebral vascular impairment, a rigid brace may be the best remedy available. However, if the muscles still display some proprioception with some neurological connections to the brain in sufficient amount that the muscles respond positively to physical therapy in such a way that the paralysis of the limbs involved diminishes and muscle tone improves then the patient may achieve substantial benefit from the device embodying the inventions described herein.

With the foot brace of this invention, the foot brace is fitted to the foot to substantially correct the foot position to approximate normal alignment of the ankle and foot bones. The foot brace is rigid laterally, but flexible front to back to allow front to back angular movement between the foot and ankle bone as the foot and leg travel through their ordinary paths of movement and thereby enable the patient to improve tone of the muscles associated with angular movement between the foot and ankle and avoid muscle atrophy.

SUMMARY OF THE INVENTION

Accordingly, it is an object of this invention to provide a foot brace which holds a patient's foot in a substantially fixed corrective position laterally, but in a flexure position front to back to thereby apply pressure to the foot and cause transmission of repeated sensory stimuli to the brain as the foot is repeatedly moved through its path of movement in a walking trajectory, which stimuli indicate to the patient a normal positioning and movement path of the foot and thereby fortify normal movement and positioning alignment of the foot as movement is repeated.

It is another object of the invention to provide such a foot brace which holds the patient's foot laterally fixed, but which is flexible front to back to accommodate front to back angular movement between the ankle and foot and extends upward and around a portion of the leg above the ankle where it is held in position by binding means.

It is another object of the invention to provide a foot brace which holds the patient's foot laterally fixed, but which is flexible to accommodate angular movement of the various parts of the foot and ankle front to back and extends upward and around a portion of the leg above the ankle where it is held in place by adjustable binding means for permitting adjustment of the binding pressure of the foot brace on the leg.

It is still another object of the invention to provide a foot brace to be worn by the patient inside a shoe which brace together with the shoe holds the patient's foot laterally fixed, but in a flexure position front to back and thereby applies pressure to the foot which causes transmission of repeated sensory stimuli to the brain as the foot is repeatedly moved through its trajectory of walking movement, which stimuli indicate to the patient a normal positioning and movement path of the foot and thereby fortify normal movement and positioning alignment of the foot as movement is repeated.

It is still another object to provide a foot brace of the type described which can be manufactured at relatively low cost.

The invention consists of certain novel features and a combination of parts hereinafter fully described, illustrated in the accompanying drawings, and particularly defined in the appended claims, it being understood that various changes in the details may be made without departing from the spirit, or forsaking any of the advantages of the present invention.

THE DRAWINGS

These and other advantages of the invention will become apparent from the following description when read in connection with the accompanying drawings in which:

FIG. 1 is a perspective view of one embodiment of the foot brace of this invention showing its relationship to the foot and shoe of a wearer.

FIG. 2 is a fragmentary front view of the mid-portion of the foot brace shown in FIG. 1.

FIG. 3 is a cross-sectional view taken along the line 3—3 of FIG. 1.

FIG. 4 is a front view of the patient's foot to indicate the preferred angular relationship of the angle and leg of the wearer.

FIG. 5 is a side view of the foot brace in the process of its manufacture.

DETAILED DESCRIPTION

In the preferred embodiment of the invention as shown in FIGS. 1 and 2, the foot brace 1 is provided with a heel cup 2 having a rounded rear wall 3 connected between two parallel sidewalls 4 and 5 and a horizontal foot rest portion 6 as a single integral piece. The connecting portions of the walls are preferably rounded to conform to the shape of the wearer's heel and foot. The heel cup 2 has a generally U-shape and preferably extends forwardly short of the ball of the foot related to the large toe. This allows maximum support and lateral restraint of the foot without impairing toe flexure as required for walking.

Secured to the sidewalls by means of fasteners 7 are upwardly extending flexible hinges 8 and 9 which are connected at their upper ends by other fasteners 7a to opposite sides of a clamping means or C-shaped support brace portion 10 curved to approximate the curvature of the wearer's leg immediately above the ankle and open in front to terminate in two front edge portions 11a and 11b. One of the fasteners 7a is shown in detail in FIG. 3. It consists of an internally threaded headed tube 7b into which an externally threaded screw 7c is tightened to securely hold the hinge 9 against the wall of the upper brace portion 10. The other fasteners 7a and 7 may be constructed the same way. The hinge itself may be made of flexible Nylon, polypropylene, or other flexible materials.

Although the hinges 8 and 9 individually are flexible, when in place on the completed brace 1, they are only free to flex front to back. Because they are connected as they are to the rigid heel cup 2 and the upper portion 10, it is evident that they are restrained from lateral flexure.

The heel cup 2 is preferably a single molded plastic piece, but it may also be assembled from its various components and joined by suitable means, such as glue. Also, the heel cup 2 and the upward extending hinges 8 and 9 may be molded as a single integral piece along with the upper brace portion 10.

A flexible strap 12, secured at one end to the upper brace portion 10 by a rivet 13 or other fastener means, is positioned to cover the front portion of the upper brace portion 10 across the edge portions 11a and 11b. The free end of the strap 12 is passed through a loop or buckle 14 so it can be tightened and drawn back upon itself and secured in the tightened position to hold the upper brace portion 10 snuggly in position against the wearer's leg. The strap 12 shown may be manufactured of a woven and molded hook and loop material, such as that sold under the trademark "VELCRO", but other conventional buckles which prevent slippage of the strap when tightened can be used. For comfort, padding 23 is folded over the upper end of the portion 10 and glued in place to pad it internally. A separate pad 23a is attached to the strap 12 to fill the gap between the edge portions 11a and 11b.

FIG. 1 also shows the relationship of the wearer's foot 15 and the wearer's shoe 16 while wearing the foot brace 1. It is intended that the shoe be worn with the foot brace to retain the heel cup position of the foot brace 1 snugly on the wearer's foot and coordinate with the function of the foot brace. Otherwise, the device requires other means to hold the brace 1 in proper contacting position with the bottom of the foot.

It is important that the flexible strap 12 be positioned immediately above the ankle for optimum results because all of the ligaments and nerves connected to the foot and ankle portions extend in close proximity through that portion of the leg. It is believed that the sensation of movement of the various portions of the foot and ankle become amplified to the wearer through the constraining pressure applied by the strap 12 in that leg region to enhance any proprioception of nerve signals or stimuli to the wearer's brain and thereby hasten or insure recovery of the wearer from any paralytic condition. In fact, sometimes the proprioception is so slight that, without the strap 12 tightened in place, the patient may perceive little or no sense of where the foot is in space. Tightening of the strap 12 enhances the sense of feeling enough to reestablish cognizance of the location of the foot and thereby enhances the wearer's ability to overcome the paralysis. Experimental results also show that improvement of the foot and ankle condition alone at those extremities of the body causes improvement in other higher reaches of the body affected by the vascular impairment. Initially, a patient with only small proprioception might have to tighten the strap 12 very tightly to be effective. Thereafter, as proprioception is enhanced and improved muscle tone develops, the patient may loosen the strap as necessary to eliminate discomfort as the sense of feeling returns or becomes stronger.

The foot brace heel cup 2 may be preformed in standard graded sizes corresponding to what might be ordinary foot sizes and foot and ankle bone placement. Such a foot brace might be satisfactory in many cases or at least as a sampler to determine if the patient's condition might respond to the preferred fitted or tailored brace. However, when the patient's neutral or normal foot and ankle bone alignment is sufficiently different than what might be considered normal, such as, when the calcaneal alignment of the heel with the leg is angled too much, the heel cup 2 should preferably be made from a cast of the patient's foot in the patient's neutral foot position as it might have been before the impairment. When worn, the foot brace will then tend to hold or urge the foot in what was the proper previously normal foot position. If properly fit, the proprioception feedback from foot movement through the applied pressure of the strap 12 will then provide an amplified feeling or signal to the wearer and his brain of the proper or normal foot movement and thereby enhance or speed recovery.

In order to cast the patient's foot in the neutral foot position, the patient preferably rests in a sitting position with the foot flatly resting on the floor as indicated in FIG. 4. The heel and toes are pressed into flat contact with the floor, but the inside arch of the foot must be elevated to a normally arched position with the aid of a pad if necessary. Without the arch, the foot may tend to turn out laterally. The foot is then wrapped with wet plaster fabric and held in this neutral position until the plaster hardens. Ordinarily, best results are achieved with the brace 1 when the cast is made with a neutral position represented by the heel bone (calcaneus) vertically aligned with the leg or at a maximum angle of about four degrees inwardly from the vertical between the ankle and the foot represented by the angle A in FIG. 4. When hardened, the cast is slit and removed from the foot. Thereafter, a plaster model is made from the plaster cast. This is accomplished by lubricating the inner surfaces of the plaster cast to prevent sticking and filling the plaster cast with wet plaster which, when hardened, will correspond to the shape of the patient's foot and ankle in the neutral position. The plaster cast is then used to form the brace 1. As indicated in FIG. 5., the plaster model 17 is wrapped with a heated sheet of polypropylene 18 which is formed into a closed bag shape around the model 17. The end 19 is wrapped around the air inlet end of a suction motor 20 fitted with an evacuation tube 21 inserted into the plaster cast 17. Operation of the motor 20 causes air to be evacuated from the cast and from around it by its porous nature which thereby causes the polypropylene sheet 18 to hug the model 17 and conform to its shape which is the same shape as the foot of the patient. While under suction, the polypropylene sheet 18 is allowed to harden. It is then removed as a single piece from the model 17 by slitting it and the excess material is trimmed by hand to create the shape of the brace shown in FIG. 1. The brace 1 is then divided into its two main parts, the heel cup 2 and the upper brace portion 10, by cutting away material and creating the space 1a between the upper portion 10 and the heel cup 2. Prior to applying the heated polypropylene sheet to the model, the hinges 8 and 9 are glued in place on the sheet to insure proper positioning of the hinges in the final brace. Pieces of felt are applied to temporarily cover the hinges 8 and 9 to insure spacing of the hinges from the ankle of the patient when the felt pieces are later removed to provide depressions or recesses 22 which appear as bulges 22a on the outsides of the brace portions.

The rear portions of the brace 1 are provided with pads 1b and 1c which act as stops when the brace is pivoted on the hinges 8 and 9 to prevent overlapping of the upper and lower portions of the brace 1. The pads 1b and 1c are easily formed by applying pads of heated polypropylene to the polypropylene sheet 18 when forming the brace around the model 17. Although not shown, soft padding can be applied to the faces of the pads 1b and 1c facing each other to eliminate intermittent bumping noises as the brace repeatedly pivots back and forth in use.

The preferred embodiment and the invention have been described to enable a person skilled in the art to make and use the same. The following claims particularly point out and distinctly claim the subject matter of the invention.

What is claimed is:

1. The combination in a foot brace for correcting foot deformation due to cerebral vascular impairment comprising a heel cup for closely embracing the heel and portions of the foot ahead of it and having an upper edge, a clamping means for engaging the leg region immediately above the ankle of the foot and having a lower edge, and two connecting means respectively disposed on opposite sides of the ankle, each of said connecting means including a hinge formed of a single piece of relatively stiff material having limited flexibility and having ends respectively fixedly secured to said heel cup and to said clamping means for interconnecting same so as to provide a space between said upper and lower edges to permit but limit front-to-back flexing of the ankle, whereby the resistance provided by the stiffness of said hinges intensifies the pressure of said heel cup against the portions of the foot ahead of the heel and said clamping means applies pressure to the leg region to enhance the wearer's feeling of angular movement between the foot and ankle.

2. The combination of claim 1 characterized by said clamping means positioned to clamp against opposite sides of the leg and provided with adjustable means for adjusting the clamping pressure against the leg.

3. The combination of claim 1 characterized by said clamping means positioned to clamp against opposite sides of the leg and provided with adjustable means for adjusting the clamping pressure against the leg, said adjustable means comprising a flexible binder which encircles at least a portion of the clamping means and is adjustable in length to vary the clamping pressure of the clamping means against the leg.

4. The combination of claim 1 characterized by said clamping means positioned to clamp against opposite sides of the leg and provided with adjustable means for adjusting the clamping pressure against the leg, said adjustable means comprising a flexible binder which encircles at least a portion of the clamping means and is adjustable in length to vary the clamping pressure of the clamping means against the leg, and said flexible binder having locking means for locking the binder in any adjusted length.

5. The combination of a foot brace to be worn inside a shoe for correcting foot deformation due to cerebral vascular impairment comprising a heel cup for closely embracing the heel and portions of the foot ahead of it and having an upper edge, a clamping means for engaging the leg region immediately above the ankle of the foot and having a lower edge, and two connecting means respectively disposed on opposite sides of the ankle, each of said connecting means including a hinge formed of a single piece of relatively stiff material having limited flexibility and having ends respectively fixedly secured to said heel cup and to said clamping means for interconnecting same so as to provide a space between said upper and lower edges to permit but limit front-to-back flexing of the ankle, whereby the resistance provided by the stiffness of said hinges intensifies the pressure of said heel cup against the portions of the foot ahead of the heel and the shoe holds said heel cup in position on the foot and said clamping means applies pressure to the leg region to enhance the wearer's feeling of angular movement between the foot and ankle as the wearer's foot travels a walking trajectory.

6. The combination of claim 5 characterized by said clamping means positioned to clamp against opposite sides of the leg and provided with adjustable means for adjusting the clamping pressure against the leg.

7. The combination of claim 5 characterized by said clamping means positioned to clamp against opposite sides of the leg and provided with adjustable means for adjusting the clamping pressure against the leg, said adjustable means comprising a flexible binder which encircles at least a portion of the clamping means and is adjustable in length to vary the clamping pressure of the clamping means against the leg.

8. The combination of claim 5 further characterized by said clamping means positioned to clamp against opposite sides of the leg and provided with adjustable means for adjusting the clamping pressure against the leg, said adjustable means comprising a flexible binder which encircles at least a portion of the clamping means and is adjustable in length to vary the clamping pressure of the clamping means against the leg and said flexible binder having locking means for locking the binder in any adjusted length.

9. The combination in a foot brace to be worn inside a shoe for correcting foot deformation due to cerebral vascular impairment comprising a heel cup having an upper edge and cast to the shape of the wearer's foot corresponding to the wearer's approximate neutral foot position as it was before the impairment for closely embracing the heel and portions of the foot ahead of it, a clamping means for engaging the leg region immediately above the ankle of the foot and having a lower edge, and two connecting means respectively disposed on opposite sides of the ankle, each of said connecting means including a hinge formed of a single piece of relatively stiff material having limited flexibility and having ends respectively fixedly secured to said heel cup and to said clamping means for interconnecting same so as to provide a space between said upper and lower edges to permit but limit front-to-back flexing of the ankle, said connecting means cooperating with said heel cup and said clamping means to resist lateral angular movement between the ankle and foot but to allow such angular movement in a front-to-back direction against the stiffness of said connecting means, whereby the shoe holds said heel cup in position on the foot and said clamping means applies pressure to the leg region to enhance the wearer's feeling of angular movement of the foot and ankle as the wearer's foot travels a walking trajectory and senses resistance to front-to-back movement of the foot provided by the stiffness of said connecting means.

10. The combination of claim 9 characterized by said clamping means positioned to clamp against opposite sides of the leg and provided with adjustable means for adjusting the clamping pressure against the leg.

11. The combination of claim 9 characterized by said clamping means positioned to clamp against opposite sides of the leg and provided with adjustable means for adjusting the clamping pressure against the leg, said clamping means being a strap of "VELCRO" material connected at one end to one side of said clamping means and passing through a loop connected to the other side of said clamping means, whereby said strap can be drawn through the loop and reversed upon itself as said adjustable means.

12. The combination of claim 9 characterized by said hinges being positioned in recesses in the walls of the foot brace to provide clearance between said connecting means and the wearer's ankle.

13. The combination of claim 9 characterized by said hinges being positioned forward of the rear of the foot brace and rearwardly of the front of the foot brace, whereby repeated front-to-back angular movement between said heel cup and said clamping means permits said upper edge of said heel cup and said lower edge of said clamping means to intermittently abut, and thickened pad means on each of said edges to prevent bypass of the said edges during said repeated angular movement.

14. The combination of claim 13 further characterized by said thickened pad means being of soft padding in the regions they abut in order to minimize sound when they abut.

* * * * *